United States Patent
Goeke

(10) Patent No.: US 7,060,664 B2
(45) Date of Patent: Jun. 13, 2006

(54) ORGANIC COMPOUNDS

(75) Inventor: Andreas Goeke, Dübendorf (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 10/497,323

(22) PCT Filed: Dec. 4, 2002

(86) PCT No.: PCT/CH02/00657

§ 371 (c)(1),
(2), (4) Date: Jun. 1, 2004

(87) PCT Pub. No.: WO03/048285

PCT Pub. Date: Jun. 12, 2003

(65) Prior Publication Data

US 2005/0119157 A1    Jun. 2, 2005

(30) Foreign Application Priority Data

Dec. 7, 2001 (EP) ................................ 011290939

(51) Int. Cl.
*C11D 3/50* (2006.01)
*A61K 8/30* (2006.01)
*C07D 241/10* (2006.01)
*C07C 43/03* (2006.01)

(52) U.S. Cl. .................... 510/106; 512/22; 544/224; 546/2; 568/820

(58) Field of Classification Search ............... 510/104, 510/105; 512/14–19; 585/361
See application file for complete search history.

(56) References Cited

U.S. PATENT DOCUMENTS

| 4,354,043 A | 10/1982 | Belko et al. ............ 568/445 |
| 4,357,949 A | 11/1982 | Klemarczyk et al. ....... 131/276 |

FOREIGN PATENT DOCUMENTS

| DE | 3410489 | * 10/1985 |
| EP | 0 040 894 | 5/1981 |
| WO | WO 86/03191 | 5/1986 |

OTHER PUBLICATIONS

B. Byrne, et al: "Photochemistry of 7-*syn*-Isobutylnorborn-2-en-2-yl Methyl Ketone." Journal of the Chemical Society, Perkin Transactions 1, No. 12, 1978, pp. 1550-1560, XP002195122.

Chemical Abstracts, vol. 92, No. 10, 1980; Columbus, Ohio, US; Abstract No. 82182x, Opdyke DLJ: "Monographs on fragrance raw materials", p. 373, col. 1; XP002195126.

Chemical Abstracts, vol. 123, No. 19, 1995; Columbus, Ohio, US; Abstract No. 255896x, Goverdhan Mehta, et al: "Electrostatic or oribtial-controlled side differentiation of pi-electron systems", p. 255895, col. 1; XP002195127.

T. Hudlicky, et al: "Synthesis of (+/−) Coronafacic Acid", Journal of the American Chemical Society, vol. 102, 1980, pp. 6353-6355; XP002195123.

M.R. Mazur, et al: "Formal Kinetic Proof of Reversible Unimolecular Transformation to a Biradical as an Obligatory First Step in the Mechanism of Cycloaddition of 5-Isopropylidenebicyclo[2.1.0]pentane to Olefins", Journal of the American Chemical Society, vol. 104, No. 8, 1982, pp. 2217-2222; XP002195124.

Godverhan Mehta, et al: "Pi-Face selectivities in nucleophilic additions to 2-*endo*-arylnorbornan-7-ones", Journal of the Chemical Society, Perkin Transactions I, vol. 22, 1996, pp. 2665-2667; XP002195125.

International Search Report for PCT/CH02/00657 dated Mar. 17, 2003.

* cited by examiner

*Primary Examiner*—John R. Hardee
(74) *Attorney, Agent, or Firm*—Norris McLaughlin & Marcus PA

(57) ABSTRACT

Bicyclo[2.2.1]heptanes or heptenes mono-substituted at the 7-position with a substituent selected from the group consisting of linear or branched $C_{2-10}$ alkyl or alkenyl, and alkylidene, and fragrance compositions containing same.

8 Claims, No Drawings

ORGANIC COMPOUNDS

This invention is concerned with certain 7-substituted bicyclo[2.2.1]heptanes and heptenes that are fragrant compounds and in particular with such compounds displaying woody, floral, hesperidic and green notes.

The invention provides in a first aspect a fragrance composition comprising bicyclo[2.2.1]heptanes or heptenes mono-substituted at the 7-position with a substituent selected from the group consisting of linear or branched $C_{2-10}$ alkyl or alkenyl, and alkylidenyl, e.g. linear or branched $C_{1-10}$ alkylidenyl. The use of these compounds in fragrance applications has heretofore not been reported in the literature. Depending on the substitution pattern of the compounds, the odours of the compounds may change throughout a broad olfactory spectrum covering woody, floral, hesperidic and green notes, and they all are interesting additional molecules in the palettes of perfumers.

Substantially all of the bicyclo[2.2.1]heptanes or heptenes hereinabove mentioned have never been reported in the literature. Accordingly, the invention provides in another of its aspects the bicyclo[2.2.1]heptanes or heptenes mono-substituted at the 7-position with a substituent selected from the group consisting of alkyl, alkenyl and alkylidene with the proviso that 7-Isopropylidene-bicyclo[2.2.1]heptane-2-carboxylic acid methyl ester; 7-Isopropylidene-bicyclo[2.2.1]heptane-2-carbonitrile; 7-isobutylbicyclo[2.2.1]hept-2-ene-2-carbonitrile; 7-isopropylidene[2.2.1]hept-5-ene-3-carbonitrile; and 1-(7-Isobutyl-bicyclo[2.2.1]hept-2-yl)-ethanone are excluded.

Compounds of the general formula (I)

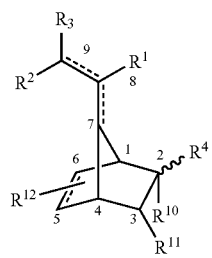

wherein,
$R^1$ is hydrogen or $C_{1-6}$ alkyl;
$R^2$ is hydrogen, $C_{1-6}$ alkyl, or $C_{2-6}$ alkenyl;
$R^3$ is hydrogen, or $C_{1-4}$ alkyl; or,
$R^1$ and $R^3$ together with the carbon atoms to which they are attached form a 5- or 6-membered carbocyclic ring;
$R^4$ is a nitrile group, 2-, 3-, or 4-pyridinyl, pyrazinyl, or a carbonyl group $COR^5$, a group $C(R^7)_2$—$OR^8$, or an oxime or oxime ether group $C=NOR^{13}$;
$R^5$ is hydrogen, $C_{1-5}$ alkyl, $C_{2-5}$ alkenyl, or $OR^6$;
$R^6$ is $C_{1-5}$ alkyl; or $C_{2-5}$ alkenyl;
$R^7$ independently are hydrogen, or $C_{1-4}$ alkyl;
$R^8$ is $C_{1-5}$ alkyl, $C_{2-5}$ alkenyl, or a carbonyl group $COR^9$;
$R^9$ is $C_{1-4}$ alkyl, $C_{2-5}$ alkenyl, or $OR^6$;
$R^{10}$ is hydrogen, or $C_{1-4}$ alkyl; $R^{11}$ is hydrogen, or linear or branched $C_{1-4}$ alkyl;
$R^{12}$ is hydrogen, or $C_{1-4}$ alkyl;
$R^{13}$ is hydrogen, or $C_{1-4}$ alkyl;

the bonds between C7 and C8 and between C8 and C9 may both be single bonds, or the dotted line together with the bond between C7 and C8, or between C8 and C9 may represent a double bond; and the bond between C5 and C6 is a single bond or, together with the dotted line, it may represent a double bond when $R^4$ is the group $C(R^7)_2$—$OR^8$, are particularly preferred compounds.

As used herein, the terms "alkyl" "alkyenyl" and "alkylidenyl" used in relation to compounds or compositions of the invention have the following preferred meanings, as appropriate: As alkyl there can be mentioned methyl, ethyl, n-propyl, iso-propyl, or linear or branched butyl, pentyl or hexyl; as alkenyl there can be mentioned vinyl, allyl or linear or branched butenyl or pentenyl; and as alkylidenyl there can be mentioned methylidenyl, ethylidenyl or propylidenyl groups, or unsymmetrically substituted alkylidene groups.

In a preferred embodiment, the substituent $R^{12}$ is bound to the ring carbon atom at $C_5$ or $C_6$.

The compounds of the present invention may contain one or more chiral centres and as such they may exist as a mixture of enantiomers and diastereomers, or they may be resolved as enantiomerically and diastereomerically pure forms. However, resolving stereoisomers adds to the complexity of manufacture and purification of these compounds and so it is preferred to use the compounds as mixtures of their stereoisomers simply for economic reasons. However, if it is desired to prepare pure stereoisomers, this may be achieved according to methodology known in the art.

Particularly preferred compounds of the present invention are represented by the formulae

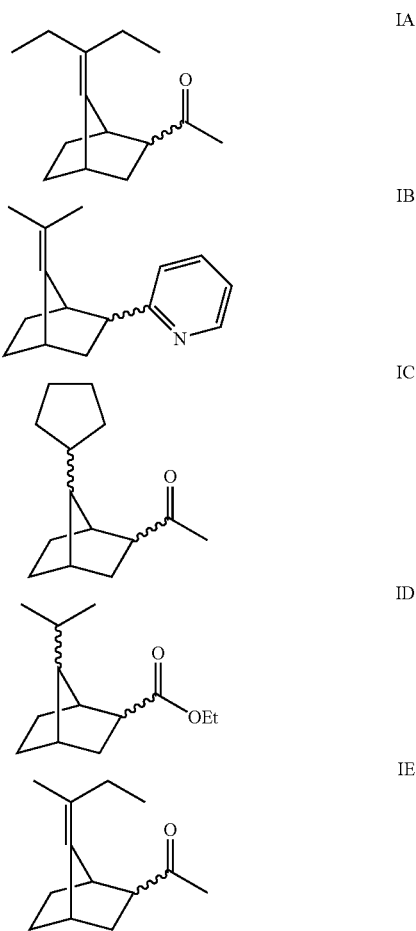

-continued

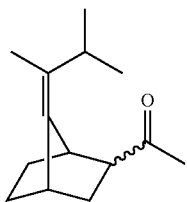

IF

The compound of the formula IA has a lilial-vertofix-type note; IB displays a petigrain-green-type note; IC displays a peppery-woody-type note; ID has an apple, myrtille and blackberries-like note; IE is linalool-woody-like; and IF has a woody-floral note.

Due to the broad odour spectrum which, depending on the substitution pattern, these compounds possess, they may be employed in a range of possible applications in practically all fields of perfumery, for example in fine perfumery, or in perfumed products of all kinds, for example luxury perfumes, cosmetic articles, consumer healthcare products or household products, e.g. washing agents, detergents and soaps.

In these applications the compounds, and in particular the compounds of formula (I) may be used alone or in admixture with other fragrances. Preferably however, the compounds are admixed with other fragrance molecules. When used in admixture with other fragrance compounds in a fragrance composition, the compounds of the present invention may be employed in varying amounts depending on the particular fragrance accord sought, e.g. from 0.1 to 99.9% by weight of the fragrance composition.

The use of a compound of the present invention in this regard is not limited to any particular perfume type nor to any special olfactory direction, odourant or class of substance. Thus, the compounds of the present invention may be mixed with, for example, ethereal oils and extracts, e.g. castoreum, costus root oil, oak moss absolute, geranium oil, jasmin absolute, patchouli oil, rose oil, sandalwood oil or ylang-ylang oil;

alcohols, e.g. citronellol, Ebanol, eugenol, geraniol, Super Muguet, linalool, phenylethyl alcohol, Sandalore, terpineol or Timberol;

aldehydes and ketones, e.g. α-amylcinnamaldehyde, Georgywood, hydroxycitronellal, Iso E Super, Isoraldeine, Hedione, maltol, methyl cedryl ketone, methylionone or vanillin;

ether and acetals, e.g. Ambrox, geranyl methyl ether, rose oxide or Spirambrene;

esters and lactones, e.g. benzyl acetate, cedryl acetate, Cyclomusk, γ-decalactone, Helvetolide, γ-undecalactone or vetivenyl acetate;

macrocycles, e.g. ambrettolide, ethylene brassylate or Exaltolide; and heterocycles, e.g. isobutylchinoline.

In addition to their admixture with other fragrances compounds, the compounds of the present invention may be admixed with one or more ingredients or excipients conventionally used in conjunction with fragrances in fragrance compositions, for example carrier materials, and other auxiliary agents commonly used in the art.

The compounds of the present invention may be added to fragrance compositions as neat ingredients, or they may be incorporated into delivery vehicles well known in the art.

For example, the compounds may be encapsulated in encapsulating media according to known techniques such as spray drying, coacervation, extrusion or coating.

The proportions in which fragrance compositions of the present invention are employed in consumer product compositions according to the present invention may vary within a large range of values and will depend upon the nature of the composition one intends to perfume, for example the nature of co-ingredients, and the particular effect that the perfumer seeks. Generally however, one may employ up to about 30% by weight in fine fragrances and up to about 50% by weight in other perfumed products.

A Method of preparing compounds hereinabove described also provides an additional aspect of the present invention. Thus, compounds as hereinabove described may be prepared according to a process wherein appropriately substituted fulvenes are reacted with, appropriately substituted dienophiles, such as α,β-unsaturated ketones or esters, or vinylpyridines under well known Diels-Alder conditions to provide bicyclo[2.2.1]heptenes of the present invention, which may be further hydrogenated, e.g. at room temperature using a palladium on charcoal catalyst, or reduced and esterified according to conventional syntheses to provide additional compounds of the present invention.

The appropriately substituted fulvenes are either commercially available or can be easily synthesised from cyclopentadiene, or an alkylated cyclopentadiene, e.g. methyl cyclopentadiene using a base such as pyrollidine and an appropriately substituted carbonyl compound such as a ketone, in alcoholic media according to techniques well known in the literature.

The appropriately substituted dienophiles for obtaining compounds of the present invention are either commercially available or can be easily synthesised with readlily available starting materials.

Further particulars as to reaction conditions are provided in the examples.

There now follows a series of examples that serve to illustrate the invention.

EXAMPLE 1

1[7-(1-Ethyl-propylidene)-bicyclo[2.2.1]hept-2-yl] ethanone

A mixture of 6,6-diethyl-fulvene (prepared as described in *J. Org. Chem.*, 1990, 55, 3395; 86.0 g, 0.64 mol) and methyl-vinyl-ketone (44.9 g, 0.64 mol) was stirred for 5 h at 50° C. The mixture was cooled to room temperature and diluted with toluene/hexane (1/9, 600 ml). The solution was hydrogenated at normal pressure using palladium on charcoal (10%) as a catalyst. After 5 h the mixture was filtered, concentrated in vacuo and the residue was distilled (bp. 70° C./0.01 Torr) to yield the title compound (65.5 g, 50%) as a mixture of 2 isomers in a ratio of 3:1. Odor description: Woody, floral, Vertofix, Lilial, ambery.

$^1$H-NMR (CDCl$_3$, 400 MHz): (major isomer) 2.98 (t, J=4.4 Hz, 1H, 1-H), 2.87–2.81 (m, 1H, 2-H), 2.61 (t, J=4.4 Hz, 1H, 4-H), 2.15 (s, 3H, COCH$_3$), 2.13–1.97 (m, 4H, =C(CH$_2$CH$_3$)$_2$), 1.87 (dd, J=12.1 Hz, 5.0 Hz, 1H, 3-H$_n$), 1.55–1.20 (m, 5H, 3-H$_x$, 5-H, 6-H), 1.02–0.88 (m, 3H, =C(CH$_2$CH$_3$)$_2$) ppm. GC/MS (EI): (major isomer): 206 (M$^+$, 22), 177 (12), 163 (32), 148 (43), 135 (45), 107 (83), 93 (62), 79 (69), 43 (100); (minor isomer): 206 (M$^+$, 13), 177 (8), 163 (66), 148 (22), 135 (37), 107 (93), 93 (50), 79 (60), 43 (100). IR (atr): 2960s, 2870s, 1708vs, 1463m, 1357m, 1172s, 840w cm$^{-1}$.

EXAMPLES 2–9

The following compounds were prepared according to the synthetic procedures of example 1 from correspondingly substituted starting materials:

endo-1-(7-Isopropylidene-bicyclo[2.2.1]hept-2yl)-ethanone

Odor description: Rosy, Peonile, apple cyclamen, fresh, woody. $^1$H-NMR (CDCl$_3$, 400 MHz): 2.98 (t, $J_{1,5x}=J_{1,2}=4.5$ Hz, 1H, 1-H), 2.86–2.81 (m, $J_{2,1}=4.5$ Hz, $J_{2,3n}=5.0$ Hz, J=2.0 Hz, 1H, 2-H), 2.61 (t, $J_{4,3x}=J_{4,5x}=4.5$ Hz, 1H, 4-H), 2.15 (s, 3H, COCH$_3$), 1.86(dd, $J_{3n,3x}=12.1$ Hz, $J_{3n,2}=5.0$ Hz, 1H, 3-H$_n$), 1.70 (s, 3H, C(CH$_3$)$_a$(CH$_3$)$_b$), 1.65 (s, 3H, C(CH$_3$)$_a$ (CH$_3$)$_b$), 1.55–1.20 (m, 5H, 3-H$_x$, 5-H, 6-H) ppm. GC/MS (EI): 178 (M$^+$, 25), 163 (6), 135 (34), 120 (60), 107 (100), 93 (92), 91 (96), 79 (50), 43 (59). IR (atr): 2955s, 2871m, 1706vs, 1447m, 1357s, 1173s, 959w cm$^{-1}$.

1-(7-sec-Butylidene-bicyclo[2.2.1]hept-2-yl)-ethanone

4 Isomers in a ratio of 1:1.5:2.9:2.8. Odor description: Woody, floral, linalool, Vertofix, ambery. $^1$H-NMR (CDCl$_3$, 400 MHz): 3.01–2.44 (m, 3H), 2.15/2.11/2.10 (4s, 3H), 2.11–2.82 (m, 3H), 1.69/1.65/1.63/1.62 (4s, 3H), 1.65–1.20 (m, 5H), 1.02–0.91 (m, 3H) ppm. GC/MS (EI): (major isomer): 192 (M$^+$, 16), 163 (9), 149 (48), 134 (41), 121 (57), 107 (54), 93 (92), 79 (52), 43 (100). IR (atr): 2960s, 2870m, 1707vs, 1453w, 1356m, 1172s, 960w cm$^{-1}$.

1-[7-(1,2-Dimethyl-propylidene)-bicyclo[2.2.1]hept-2-yl]-ethanone

4 Isomers in a ratio of 1:1:2.2:1.9. Odor description: Woody, cedary, floral, Lilial. $^1$H-NMR (CDCl$_3$, 400 MHz): 3.29–2.42 (m, 4H), 2.14/2.11/2.09 (4s, 3H), 1.88–1.81 (m, 1H) 1.60/1.55/1.53 (4s, 3H), 1.65–1.19 (m, 5H), 1.01–0.90 (m, 6H) ppm. GC/MS (EI): (major isomer): 206 (M$^+$, 24), 163 (64), 148 (36), 135 (33), 121 (76), 107 (65), 93 (75), 79 (32), 43 (100). IR(atr): 2958s, 2869m, 1708vs, 1464w, 1358m, 1173m, 1080w cm$^{-1}$.

1-[7-(1,5-Dimethyl-hex-4-enylidene)-bicyclo[2.2.1]hept-2-yl]-ethanone

4 Isomers in a ratio of 1:1.5:3:2.5. Odor description: Woody, cedary, hesperidic, fruity, floral. $^1$H-NMR (CDCl$_3$, 400 MHz): 5–15–5.04 (m, 1H), 2.96–2.43 (m, 3H), 2.26–1.83 (m,8H), 1.75–1.05 (m, 14H) ppm. GC/MS (EI): (major isomer): 246 (M$^+$, 5), 203 (7), 177 (31), 159 (9), 135 (38), 119 (25), 107 (41), 91 (40), 69 (26), 43 (100). IR (atr): 2940s, 2868s, 1708vs, 1451m, 1376w, 1356m, 1172s, 1059w, 960w cm$^{-1}$.

1-(7-Cyclohexylidene-bicyclo[2.2.1]hept-2-yl)-ethanone

2 Isomers A and B in a ratio of 1:2. Odor description: leathery, moss, capsicon, pyralone. $^1$H-NMR (CDCl$_3$, 400 MHz): 3.02 (t, J=4.4 Hz, ⅔H, 1-H$_A$), 2.90 (d, J=4 Hz ⅓H, 1-H$_B$), 2.85–2.80 (m, J=12.1 Hz, 4.8 Hz, 1.6 Hz, ⅔H, 2-H$_B$), 2.68/s.64 (2t, J=4.4 Hz, 1H, 4-H), 2.47 (dd, J=9.2 Hz, 5.2 Hz, ⅓H, 2-H$_A$), 2.14, 2.10 (2s, 3H, COCH$_3$), 2.18–2.01 (m, 4H), 1.86 (dd, J=12.1 Hz, 4.8 Hz, ⅔H, 3-H$_{An}$), 1.65–1.20 (m, 11H) ppm. GC/MS (EI): (major isomer): 218 (M$^+$, 18), 175 (54), 160 (100), 148 (59), 131 (30), 117 (38), 105 (42), 91 (92), 79 (94), 67 (44), 43 (96). IR (atr): 2922s, 2851m, 1707vs, 1447m, 1356m, 1172s, 1002w, 851w cm$^{-1}$.

1-(7-Isobutyl-bicyclo[2.2.1]hept-2-yl)-ethanone

4 Isomers in a ratio of 1.5:1:8:22. Odor description: woody, green, grapefruit, glycolierral. $^1$H-NMR (CDCl$_3$, 400 MHz): 2.98–2.83 (m, 1H), 2.40–2.32 (m, 1H), 2.16/2.14/2.11/2.10 (4s, 3H), 2.05–1.93 (m, 1H), 1.88–1.73 (m, 2H), 1.67–1.40 (m, 4H), 1.29–1.05 (m, 4H), 0.95–0.82 (m, 6H) ppm. GC/MS (EI): (major isomer): 194 (M$^+$, 4), 136 (100), 121 (54), 95 (28), 79 (25), 71 (30), 67 (48), 43 (78).

7-Isopropyl-bicyclo[2.2.1]heptane-2-carboxylic Acid Ethyl Ester

4 Isomers in a ratio of 1:35:11:16. Odor description: rhubarb, fruity, pear, green, apple. $^1$H-NMR (CDCl$_3$, 400 MHz): 4.18–4.06 (m, 2H), 2.87-2.73 (m, 1H), 2.41–2.26 (m, 2H), 2.19–2.06 (m, 1H), 1.97–1.15 (m, 10H), 0.95–0.86 (m, 6H) ppm. GC/MS (EI): (major isomer): 210 (M$^+$, 3), 164 (10), 137 (13), 122 (15), 110 (92), 101 (100), 95 (25), 81 (42), 73 (48), 41 (34). IR (atr): 2956s, 2874m, 1731vs, 1467m, 1367m, 1179vs, 1042m, 866w cm$^{-1}$.

2-(7-Isopropylidene-bicyclo[2.2.1]hept-2-yl)-pyridine

Prepared according to example 1 from dimethyl-fulvene and 2-vinyl-pyridine. 2 Isomers in a ratio of 6:4. Odor description: green, petitgrain, pickles, estragon. endo-Isomer: $^1$H-NMR (CDCl$_3$, 400 MHz): 8.58–8.56 (m, 1H, Ar—H), 7.60 (dt, J=7.6 Hz, 2.0 Hz, 1H, Ar—H), 7.22 (d, J=7.6 Hz, 1H, Ar—H), 7.10–7.07 (m, 1H, Ar—H), 3.30–3.33 (m, 1H, 2-H), 2.97 (t, J=4.4 Hz, 1H, 1-H), 2.72 (t, J=4.4 Hz, 1H, 4-H), 2.06–1.97 (m, 1H), 1.87 (dd, J=12.0 Hz, 5.6 Hz, 1H, 3-H$_n$), 1.73 (s, 3H, C=C(CH$_3$)(CH$_3$)), 1.79 (s, 3H,), 1.61–1.53 (m, 1H), 1.42–1.24 (m, 4H) ppm. GC/MS (EI): 213 (M$^+$, 3), 159 (8), 158 (5), 117 (5), 106 (100), 93 (28), 77 (7), 51 (3), 41 (4). IR (atr): 3064w, 2944vs, 2869s, 1589s, 1568m, 1472s, 1432s, 1372m, 1171m, 1146m, 790m, 747s cm$^{-1}$. exo-Isomer: $^1$H-NMR (CDCl$_3$, 400 MHz): 8.46–8.44 (m, 1H, Ar—H), 7.55 (dt, J=7.6 Hz, 2.0 Hz, 1H, Ar—H), 7.11 (d, J=7.6 Hz, 1H, Ar—H) 7.06–7.03 (m, 1H, Ar—H), 3.04 (dd, J=9.2 Hz, 5.4 Hz, 1H, 2-H), 2.75 (t, J=4.0 Hz, 1H, 4-H), 2.71 (d, J=3.2 Hz, 1H, 1-H), 1.92 (dd, J=12.4 Hz, 9.2 Hz, 1H, 3-H), 1.72 (s, 3H, C=C(CH$_3$)(CH$_3$)), 1.55 (s, 3H, C=C(CH$_3$)(CH$_3$)), 1.89–1.38 (m, 5H) ppm. GC/MS (EI): 213 (M$^+$, 8), 172 (5), 158 (60), 117 (5), 106 (100), 93 (40), 77 (9), 41 (5). IR (atr): 3063w, 2948vs, 2867s, 2726w, 1590s, 1569m, 1472, s, 1433s, 1371m, 1148m, 768m, 747s cm$^{-1}$.

EXAMPLE 10

Acetic Acid 7-isopropylidene-2,5-dimethyl-bicyclo[2.2.1]hept-5-en-2-ylmethyl Ester Step A: (7-Isopropylidene-2,5-dimethyl-bicyclo[2.2.1]hept-5-en-2-yl)-methanol A mixture of 5-isopropylidene-2-methyl-cyclopenta-1,3-diene (26.4 g, 0.22 mol) and methacroleine (29.4 g, 0.42 mol) were stirred for 2 days at room temperature. The mixture was diluted with diethyl ether (50 ml) and added dropwise at 0° C. to a suspension of LiAlH$_4$ (6.25 g, 0.16 mol) in ether (100 ml). After having been stirred for 1 h at room temperature, the mixture was dropwise quenched successively with water (6 ml), NaOH (15%, 6 ml) and water (6 ml). The mixture was filtered, concentrated in vacuo and the residue was purified by chromatography on silica gel (hexane:MTBE=9:1) to yield 21.6 g of a colorless oil.

Step B: Acetic Acid 7-isopropylidene-2,5-dimethyl-bicyclo[2.2.1]hept-5-en-2-ylmethyl Ester To a solution of (7-Isopropylidene-2,5-dimethyl-bicyclo [2.2.1]hept-5-en-2-yl)-methanol (4.32 g, 22.5 mmol), pyridine (3.55 g, 45 mmol) and DMAP (50 mg) in dichloromethane (50 ml) was added acetyl chloride (2.47 g, 31.5 mmol) with cooling. The mixture was stirred at room temperature for 1 h and was then diluted with water and extracted with pentane (3×80 ml). the organic phase was washed with 1N HCl, water and brine, dried (MgSO$_4$) and concentrated in vacuo. The residue was purified by chromatography on silica gel (hexane:MTBE=9:1) to yield 4.25 g of a colorless oil as a mixture of isomers. Odor description: cedarwood oil, carrot, verdyl, musky. $^1$H-NMR (CDCl$_3$, 400 MHz): 5.93–5.72 (m, 1H), 3.94–3.73 (m, 2H), 3.10–2.78 (m, 2H), 2.09–2.03 (m, 3H), 1.85–1.53 (m, 9H1.50–1.15 (m, 2H), 1.09/0.97/0.92/0.89 (4s, 3H) ppm. GC/MS (EI): main isomer: 234 (M$^+$, trace), 159 (3), 120 (100), 105 (46), 91 (11), 77 (7), 43 (15), IR (atr): 2927m, 2726w, 1741s, 1446m, 1369m, 1233vs, 1031s, 986m, 802m cm$^{-1}$.

EXAMPLE 11

Application

| A perfume for a detergent powder or a fabric softener | |
|---|---|
| Acetate PTBCH | 8 |
| Agrumex | 8 |
| Hexyl cinnamic aldehyde | 16 |
| Aldehyde C10 | 0.3 |
| Aldehyde C12 MNA | 0.3 |
| Methyl anthranilate | 0.3 |
| Citronellol | 5 |
| Vanilline | 0.3 |
| Cyclal C | 0.2 |
| Gardenol | 0.5 |
| Hedione | 3 |
| γ-Methyl ionone | 5 |
| Linalool | 15 |
| Myraldene | 1 |
| Orange oil | 5 |
| Methyl naphtylketone | 0.3 |
| γ-Undecalactone | 2 |
| Radjanol | 1.8 |
| Hexyl salicylate | 5 |
| Thibetolide | 3 |
| 1[7-(1-Ethyl-propylidene)-bicyclo[2.2.1]hept-2-yl-]-ethanone | 20 |
| | 100 |

In this formulation 1[7-(1-ethyl-propylidene)-bicyclo [2.2.1]hept-2-yl-]-ethanone harmonizes floral-muguet and woody facets in an a more balanced and fresher way compared to formulas in which the bicyclo[2.2.1] compound was replaced by equal amounts of lilial or vertofix or by a mixture of lilial and vertofix.

The invention claimed is:

1. A compound of the general formula wherein,
R$^1$ is hydrogen or C$_{1-6}$alkyl,;
R$^2$ is hydrogen, or C$_{1-6}$alkyl or C$_{2-6}$ alkenyl;
R$^3$ is hydrogen, or C$_{1-4}$ alkyl; or,
R$^1$ and R$^3$ together with the carbon atoms to which they are attached form a 5- or 6-membered carbocyclic ring;
R$^4$ 2-, 3-, or 4-pyridinyl, pyrazinyl, or a group C(R$^7$)$_2$—OR$^8$—;
R$^7$ independently are hydrogen, or C$_{1-4}$ alkyl;
R$^8$ is C$_{1-5}$ alkyl, C$_{2-5}$ alkenyl, or a carbonyl group COR$^9$;
R$^9$ is C$_{1-4}$ alkyl, or C$_{1-4}$ alkenyl;
R$^{10}$ is hydrogen, or C$_{1-4}$ alkyl;
R$^{11}$ is hydrogen, or C$_{1-4}$ alkyl;
R$^{12}$ is hydrogen, or C$_{1-4}$ alkyl;
R$^{13}$ is hydrogen, or C$_{1-4}$ alkyl;
the bonds between C7 and C8 and between C8 and C9 may both be single bonds, or the dotted line together with the bond between C7 and C8, or between C8 and C9 may represent a double bond; and the bond between C5 and C6 is a single bond or, together with dotted line, it may represent a double bond when R$^4$ is the group C(R$^7$)$_2$—OR$^8$.

2. A consumer product composition comprising a compound according to claim 1.

3. A consumer product composition according to claim 2 selected from fine perfumery compositions, or perfumed products selected from luxury perfumes, cosmetic articles, consumer licaitheare products or bousebold products.

4. A consumer product according to claim 3 comprising a compound according to claim 2 present in an amount ranging from 0.001% to 10% by weight.

5. A method of perfuming a consumer product composition comprising tbe step of mixing a compound as defined in claim 1 with said consumer product composition.

6. A fragrance composition comprising a compound according to claim 1.

7. A compound according to claim 1 selected from the compounds of the formulae

IB

8. A fragrance composition comprising a compound according to claim 7.

* * * * *

UNITED STATES PATENT AND TRADEMARK OFFICE
CERTIFICATE OF CORRECTION

PATENT NO. : 7,060,664 B2
APPLICATION NO. : 10/497323
DATED : June 13, 2006
INVENTOR(S) : Andreas Goeke It is certified that error appears in the above-identified patent and that said Letters Patent is hereby corrected as shown below:

Column 8, Lines 38-42, "A consumer product composition according to claim 2 selected from fine perfumery compositions, or perfumed products selected from luxury perfumes, cosmetic articles, consumer licaitheare products or bousehold products." should read -- A consumer product composition according to claim 2 selected from fine perfumery compositions, or perfumed products selected from luxury perfumes, cosmetic articles, consumer healthcare products or household products. --

Signed and Sealed this

Eighteenth Day of May, 2010

David J. Kappos
*Director of the United States Patent and Trademark Office*